United States Patent
Mroueh et al.

(10) Patent No.: US 11,645,555 B2
(45) Date of Patent: May 9, 2023

(54) FEATURE SELECTION USING SOBOLEV INDEPENDENCE CRITERION

(71) Applicant: INTERNATIONAL BUSINESS MACHINES CORPORATION, Armonk, NY (US)

(72) Inventors: Youssef Mroueh, New York, NY (US); Tom Sercu, New York, NY (US); Mattia Rigotti, New York, NY (US); Inkit Padhi, White Plains, NY (US); Cicero Nogueira Dos Santos, Montclair, NJ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 580 days.

(21) Appl. No.: 16/600,477

(22) Filed: Oct. 12, 2019

(65) Prior Publication Data
US 2021/0110285 A1    Apr. 15, 2021

(51) Int. Cl.
*G06F 17/00*       (2019.01)
*G06N 5/04*        (2023.01)
(Continued)

(52) U.S. Cl.
CPC ............... *G06N 5/04* (2013.01); *G06N 20/00* (2019.01); *G16B 20/00* (2019.02); *G16B 40/00* (2019.02)

(58) Field of Classification Search
CPC ............... G06F 16/245; G06F 16/2453; G06F 16/24547; G06N 5/04; G06N 20/00; (Continued)

(56) References Cited

U.S. PATENT DOCUMENTS 8,429,103 B1    4/2013 Aradhye et al.
8,645,119 B2    2/2014 Och et al.
(Continued)

FOREIGN PATENT DOCUMENTS

CN    107730154 A    2/2018
CN    109460825 A    3/2019

OTHER PUBLICATIONS

Pascal Kerschke and Heike Trautmann. Automated Algorithm Selection on Continuous Black-Box Problems by Combining Exploratory Landscape Analysis and Machine Learning. Evol. Comput., 27, 1 , 99-127, (Year: Mar. 2019).*

(Continued)

*Primary Examiner* — Greta L Robinson
(74) *Attorney, Agent, or Firm* — Intelletek Law Group, PLLC; Gabriel Daniel, Esq.

(57) ABSTRACT

A machine learning system that implements Sobolev Independence Criterion (SIC) for feature selection is provided. The system receives a dataset including pairings of stimuli and responses. Each stimulus includes multiple features. The system generates a correctly paired sample of stimuli and responses from the dataset by pairing stimuli and responses according to the pairings of stimuli and responses in the dataset. The system generates an alternatively paired sample of stimuli and responses from the dataset by pairing stimuli and responses differently than the pairings of stimuli and responses in the dataset. The system determines a witness function and a feature importance distribution across the features that optimizes a cost function that is evaluated based on the correctly paired and alternatively paired samples of the dataset. The system selects one or more features based on the computed feature importance distribution.

20 Claims, 7 Drawing Sheets

(51) Int. Cl.
 *G16B 20/00* (2019.01)
 *G16B 40/00* (2019.01)
 *G06N 20/00* (2019.01)
(58) Field of Classification Search
 CPC .......... G06N 3/08; G16B 20/00; G16B 40/00; G16B 40/10
 See application file for complete search history.

(56) References Cited

U.S. PATENT DOCUMENTS

| | | | |
|---|---|---|---|
| 10,621,491 B2* | 4/2020 | Vallée | G16H 50/30 |
| 11,373,760 B2* | 6/2022 | Mroueh | G06F 30/20 |
| 2017/0243317 A1* | 8/2017 | Rodriguez | G06V 20/20 |
| 2017/0290504 A1 | 10/2017 | Khaderi et al. | |
| 2018/0137219 A1 | 5/2018 | Goldfarb et al. | |
| 2019/0018897 A1 | 1/2019 | Iannaccone | |
| 2020/0086078 A1 | 3/2020 | Poltorak | |
| 2021/0057042 A1 | 2/2021 | Beaubier et al. | |
| 2021/0104321 A1 | 4/2021 | Lipsky et al. | |
| 2021/0110409 A1* | 4/2021 | Mroueh | G16B 40/00 |

OTHER PUBLICATIONS

List of IBM Patents or Applications Treated as Related. (2 pgs.), Oct. 12, 2019.

Tansey, W. et al., "The Holdout Randomization Test: Principled and Easy Black Box Feature Selection"; arXiv:1811.00645v3 [stat.ME] May 29, 2019; 26 pgs.

Burns, C. et al., "Interpreting Black Box Models via Hypothesis Testing"; arXiv:1904.00045v2 [stat.ML] Jun. 10, 2019; 17 pgs.

Bach, F. "On the Equivalence between Kernel Quadrature Rules and Random Feature Expansions"; J. of Machine Learning Research (2017); vol. 18, pp. 1-38.

Xiang, S. et al., "Semi-Supervised Classification via Local Spline Regression"; IEEE Transactions On Pattern Analysis and Machine Intelligence (2010); vol. 32:11; pp. 2039-2053.

* cited by examiner

FEATURE SELECTION USING SOBOLEV INDEPENDENCE CRITERION

BACKGROUND

Technical Field

The present disclosure generally relates to feature selection in machine learning and other applications.

Description of the Related Arts

In machine learning, feature selection is the process of selecting a subset of relevant features (e.g., variables, predictors) for use in model construction. The use of feature selection techniques is premised on the data including some features that are either redundant or irrelevant, and can thus be removed without incurring much loss of information. Feature selection techniques have several advantages: simplified models that are easier to interpret, shorter training times, avoidance of various phenomena that arise when analyzing and organizing data in high-dimensional spaces, sometimes referred to as curse of dimensionality, and enhanced generalization by reducing overfitting.

SUMMARY

Some embodiments provide a machine learning system that implements Sobolev Independence Criterion (SIC) for feature selection. The system receives a dataset including pairings of stimuli and responses. Each stimulus includes multiple features. The system generates a correctly paired sample of stimuli and responses from the dataset by pairing stimuli and responses according to the pairings of stimuli and responses in the dataset. The system generates an alternatively paired sample of stimuli and responses from the dataset by pairing stimuli and responses differently than the pairings of stimuli and responses in the dataset. The system determines a witness function and a feature importance distribution across the features that optimizes a cost function that is evaluated based on the correctly paired and alternatively paired samples of the dataset. The system selects one or more features based on the computed feature importance distribution.

In some embodiments, the machine learning system receives a set of control data having values that correspond to the multiple features. The machine learning system concatenates the control data with correctly paired stimuli and responses from the dataset in pairings according to the pairings of stimuli and responses in the dataset as a first concatenated sample. The machine learning system concatenates the control data with alternatively paired stimuli and responses from the dataset in pairings different than the pairings of stimuli and responses in the dataset as a second concatenated sample. The machine learning system determines a concatenated feature importance distribution that optimizes a cost function that is evaluated based on the first concatenated sample and the second concatenated sample. The machine learning system selects one or more features by comparing a first half of the concatenated feature importance distribution that correspond to the multiple features of the stimuli and a second half of the concatenated feature importance distribution that correspond to the multiple features of the control data.

The preceding Summary is intended to serve as a brief introduction to some embodiments of the disclosure. It is not meant to be an introduction or overview of all inventive subject matter disclosed in this document. The Detailed Description that follows and the Drawings that are referred to in the Detailed Description will further describe the embodiments described in the Summary as well as other embodiments. Accordingly, to understand all the embodiments described by this document, a Summary, Detailed Description and the Drawings are provided. Moreover, the claimed subject matter is not to be limited by the illustrative details in the Summary, Detailed Description, and the Drawings, but rather is to be defined by the appended claims, because the claimed subject matter can be embodied in other specific forms without departing from the spirit of the subject matter.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

I. Sobolev Independence Criterion

Some embodiments of the disclosure provide a computer implemented method for performing feature selection that maximizes true positive rate (TPR) while minimizes false discovery rate (FDR). Specifically, the method implements a Sobolev Independence Criterion (SIC), which is a non-linear and interpretable measure of dependency to determine feature importance of a dataset. Specifically, Sobolev space is used to determine a witness function for the dataset that promotes non-linear sparsity. The Sobolev space is also used to compute a set of importance (or influence) scores for the different features of the dataset. The witness function and/or the importance scores of the features may be used to perform feature selection with null-hypothesis testing methods that maximize TPR and minimize FDR.

Figure 1:
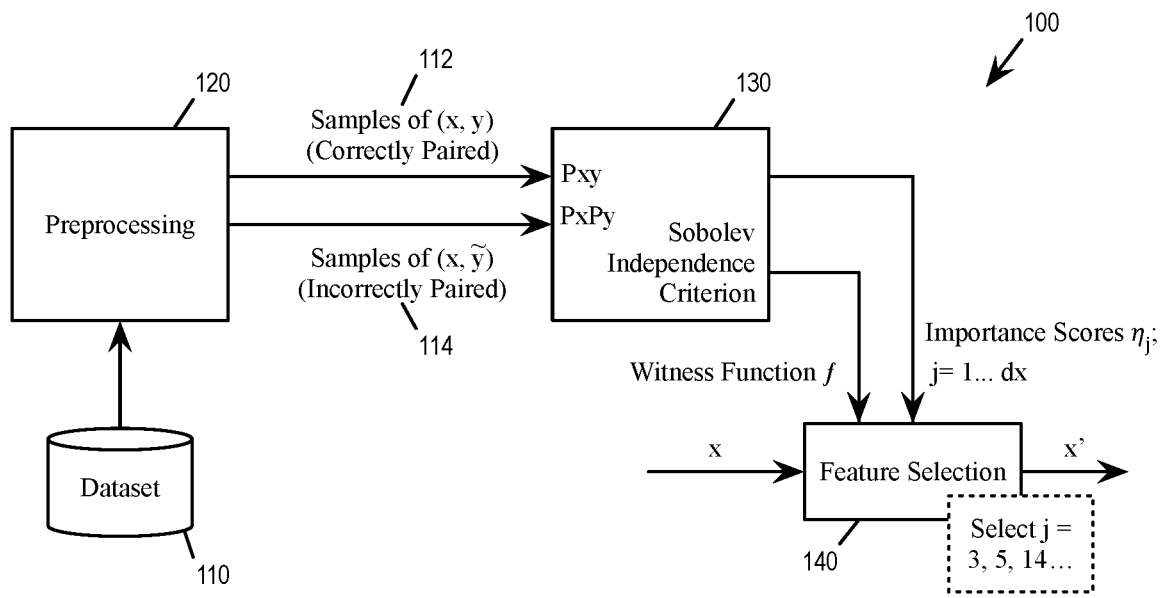
FIG. 1 conceptually illustrates using Sobolev Independence Criterion (SIC) to determine a witness function and feature importance scores for a dataset.
Figure 1:
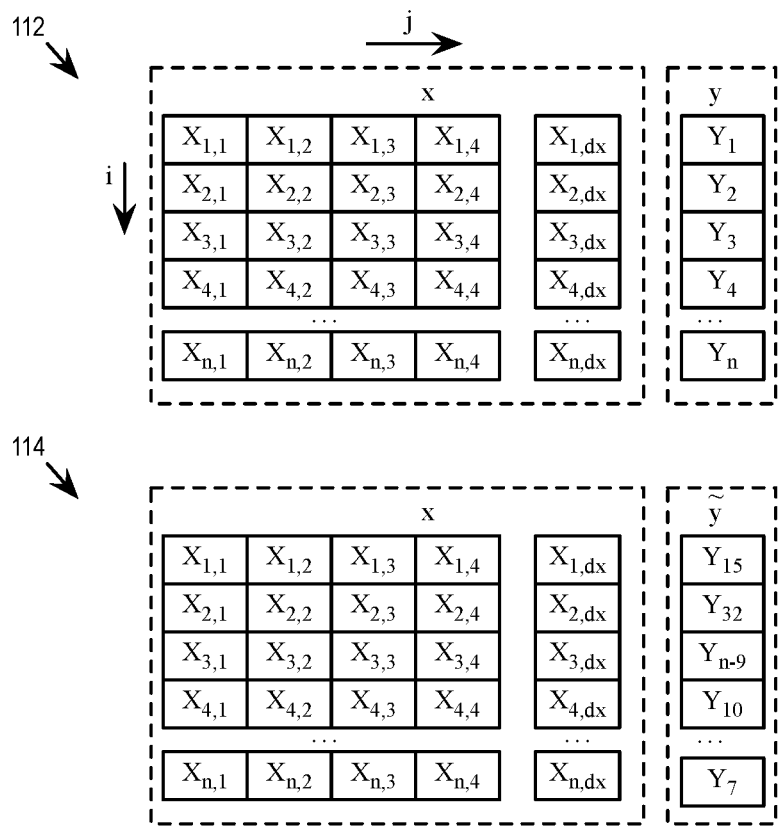

FIG. 1 conceptually illustrates using Sobolev Independence Criterion (SIC) to determine a witness function and feature importance scores for a dataset. The figure illustrates a machine learning system 100 that is trained to predict a response based on a stimulus. A dataset 110 with pairs of corresponding stimuli and responses is used to train the machine learning system 100.

The machine learning system 100 includes a preprocessing module 120, a SIC module 130, and a feature selection module 140. The preprocessing module 120 generates samples of the dataset 110 for the SIC module 130. The SIC module 130 uses the samples of the dataset to generate feature selection parameters (witness function $f$ and feature importance scores $\eta$) for the feature selection module 140. The feature selection module 140 uses the feature selection parameters to identify features in a stimulus that are sufficiently important for determining a response.

In some embodiments, the modules 120-140 are modules of software instructions being executed by one or more processing units (e.g., a processor) of a computing device or computing system. In some embodiments, the modules 120-140 are modules of hardware circuits implemented by one or more integrated circuits (ICs) of an electronic apparatus. Though the modules 120, 130, and 140 are illustrated as being separate modules, some of the modules can be combined into a single module. For example, the functionalities of the SIC module 130 can be merged into the feature selection module 140. An example computing device 800 that may implement the machine learning system 100 will be described by reference to FIG. 8 below.

The dataset 110 includes historical data of stimulus-response (or input-output) pairs. The response (y) of each pair is observed to be associated with the stimulus (x) of the pair. In some embodiments, each stimulus-response pair (or x-y pair) corresponds to an individual. The stimulus x correspond to the expression levels of a list of genes, a genetic profile, or the genome of the individual, while the response y correspond to a particular phenotype or a behavioral trait in the individual, e.g., the presence or absence of a particular disease in the individual. The features of x correspond to different genes of the genome. In other words, in one aspect, the machine learning system 100 is for identifying the genes that are influential or important in determining whether the individual may develop the particular disease. In the example, the different stimuli and their corresponding responses (e.g., individual genomes and their corresponding disease indications) are indexed by i, while the different features in a stimulus (e.g., different genes in a genome) are indexed by j. The dimension of a stimulus is dx, which correspond to the number of features in a stimulus (e.g., the number of genes in a genome). Thus, for an individual i, $x_i$ indicates the genome or stimulus, $y_i$ or $Y_i$ indicates the disease or response, $X_{i,j}$ is the value of a gene or feature.

Pairing of stimuli and responses may also represent other types of input-output relationships. For example, the stimuli may represent online content presented to individual users of an online platform and the responses may represent user preference measured in terms of click-through rate. In this case feature selection is useful to predict what to show to a user to cause the user to click on an online ad.

The preprocessing module 120 receives the dataset 110 and generates two samples 112 and 114 of the stimuli and the responses in the dataset. The first sample 112 is a correctly paired sample of stimuli and responses from the dataset 110 that can be used to generate a joint distribution of x and y, or Pxy. Each response in the correctly paired sample is paired with the same stimulus as it does in the dataset, i.e., belonging to the same individual i. The second sample 114 is an alternatively paired sample of stimuli and responses from the dataset 110 that can be used to generate a product of marginals of x and y, or PxPy. In some embodiments, each response in the second sample is randomly paired with a stimulus from the dataset. In some embodiments, the second sample is generated by randomly permutating the responses from the dataset (e.g., by shifting the positions of the $Y_i$ for different i's). The randomly permutated responses are denoted as $\tilde{y}$.

The first sample 112 and the second sample 114 are fed to the SIC module 130 at Pxy and PxPy terminals, respectively. The SIC module 130 in turn produces a witness function $f$ and a feature importance distribution $\eta$ that includes a set importance scores $\eta_j$ for different features (different j's). Specifically, the SIC module 130 implements a Sobolev Independent Criterion (SIC) that is used to evaluate how well the witness function $f$ is able to distinguish the correctly paired sample from the alternatively paired sample. In some embodiments, the Sobolev Independent Criterion (SIC) is specified according to the following:

$$SIC_{(L_1)^2} = \sup_{f \in F} \left\{ \mathbb{E}_{p_{xy}} f(x,y) - \mathbb{E}_{p_x p_y} f(x,y) - \frac{\lambda}{2}(\Omega_S(f))^2 - \frac{\rho}{2}\mathbb{E}_\mu f^2(x,y) \right\} \quad (1)$$

The optimization problem in expression (1) is to be solved for finding a witness function $f$ of x and y that optimizes (or lead to a supremum of) a cost function $$\mathbb{E}_{p_{xy}} f(x,y) - \mathbb{E}_{p_x p_y} f(x,y) - \frac{\lambda}{2}(\Omega_S(f))^2 - \frac{\rho}{2}\mathbb{E}_\mu f^2(x,y), \text{ where:}$$

$\mathbb{E}_{p_{xy}} f(x,y)$ is an expectation value of $f$ computed from the correctly paired sample;

$\mathbb{E}_{p_x p_y} f(x,y)$ is an expectation value of $f$ computed from the alternatively paired sample;

$$\frac{\lambda}{2}(\Omega_s(f))^2$$

computes a gradient sparsity; and $$\frac{\rho}{2}\mathbb{E}_\mu f^2(x,y)$$

computes an L2 penalty for regularization.

In some embodiments, the gradient sparsity term is provided by the following expression:

$$\Omega_s(f) = \sum_{j=1}^{d_x} \sqrt{\mathbb{E}_{(x,y) \sim \mu} \left| \frac{\partial f(x,y)}{\partial x_j} \right|^2} \quad (2)$$

For some embodiments, the alternatively paired sample is used to compute the gradient sparsity term ($\mu = P_x P_y$), and the expression $$\sqrt{\mathbb{E}_{(x,y) \sim \mu} \left| \frac{\partial f(x,y)}{\partial x_j} \right|^2}$$

in equation (2) is used to determine feature selection. Thus, in the cost function of Eq. (1), the gradient sparsity term has an expectation preceded by square root non-linearity. To address the non-linearity, in some embodiments, the sparsity gradient term is computed according to:

$$(\Omega_s(f))^2 = \inf \left\{ \frac{\mathbb{E}_{P_x P_y} \left| \frac{\partial f(x,y)}{\partial x_j} \right|^2 + \varepsilon}{\eta_j} : \eta, \eta_j > 0, \sum_{j=1}^{d_x} \eta_j = 1 \right\} \quad (3)$$

The $\eta_j$ for a particular feature j defines the influence (or importance) score of the feature. In some embodiments, the SIC module 130 solves optimization problem (3) to obtain $f$ and a feature importance distribution $\eta$ (i.e., $\eta_j$ for j=1 to dx) by optimizing expression (3) on $f$ and $\eta$ for $\varepsilon \to 0$. At optimum, the $\eta_j$ is provided by the following expression:

$$\eta_j = \frac{\sqrt{\mathbb{E}_{P_x P_y} \left| \frac{\partial f(x,y)}{\partial x_j} \right|^2 + \varepsilon}}{\sum_{k=1}^{d_x} \sqrt{\mathbb{E}_{P_x P_y} \left| \frac{\partial f(x,y)}{\partial x_j} \right|^2 + \varepsilon}} \quad (4)$$

To summarize, a cost function of the witness function (e.g., expression (1)) includes a gradient sparsity term and a regularization term. The gradient sparsity term is evaluated by computing a partial derivative of the witness function at each feature of the plurality of features (e.g., expression (3)) such that the determined witness function and feature importance distribution minimizes the gradient sparsity term.

In some embodiments, the SIC module 130 of the machine learning system 100 uses an empirical estimate of SIC to compute the witness function $f$ and the influence distribution $\eta$. The empirical estimate of SIC is expressed as the following:

$$\widehat{SIC} = -\inf\{\hat{L}(f,\eta): f \in \mathcal{F}, \eta_j, \eta_j > 0, \Sigma_{j=1}^{d_x} \eta_j = 1\} \quad (5)$$

Where $$\hat{L}(f,\eta) = \frac{1}{N}\Sigma_{i=1}^{N} f(x_i, \tilde{y}_i) - \frac{1}{N}\sum_{i=1}^{N} f(x_i, \tilde{y}_i) + \frac{\lambda}{2}\Sigma_{j=1}^{d_x} \frac{\frac{1}{N}\sum_{i=1}^{N} \left| \frac{\partial f(x_i, \tilde{y}_i)}{\partial x_j} \right|^2 + \varepsilon}{\eta_j} + \frac{\rho}{2}\sum_{i=1}^{N} f^2(x_i, \tilde{y}_i) \quad (6)$$

Based on Eq. (6), in some embodiments, the SIC module 130 uses a Stochastic Gradient Descent Procedure to solve for the witness function $f$ according to the following expression:

$$\theta \leftarrow \theta - \alpha_\theta \frac{\partial \hat{L}(f_\theta, \eta)}{\partial \theta} \quad (7)$$

In Eq. (7), the witness function $f$ is parametrized by a set of parameters $\theta$ as $f_\theta$, and partial derivatives of $f$ and $\eta$ are evaluated at each feature j of the plurality of features. The gradient descent is performed to ascertain $\theta$, which in some embodiments represents weights of a neural network that is being trained to implement the witness function $f$. In some embodiment, ADAM Algorithm (an optimization algorithm for updating neural network weights) is used to compute Eq. (7). The SIC module 130 also performs mirror descent to determine the influence distribution $\eta$ according to the following:

$$\text{logit} \leftarrow \log(\eta) - \alpha_\eta \frac{\partial \hat{L}(f_\theta, \eta)}{\partial \eta}; \eta \leftarrow \text{Softmax(logit)} \quad (8)$$

The logit function is the logarithm of probability. It is a type of function that creates a map of probability values. The Softmax function is normalized exponential function that takes as input a vector of K real numbers, and normalizes it into a probability distribution consisting of K probabilities proportional to the exponentials of the input numbers. For expressions (5) through (8), $\varepsilon$ is a small positive number included for numerical stability, $\lambda$ is a Lagrange multiplier, and the parameters $\rho$, $\alpha_\theta$, $\alpha_\eta$ are learning rates.

Figure 2:
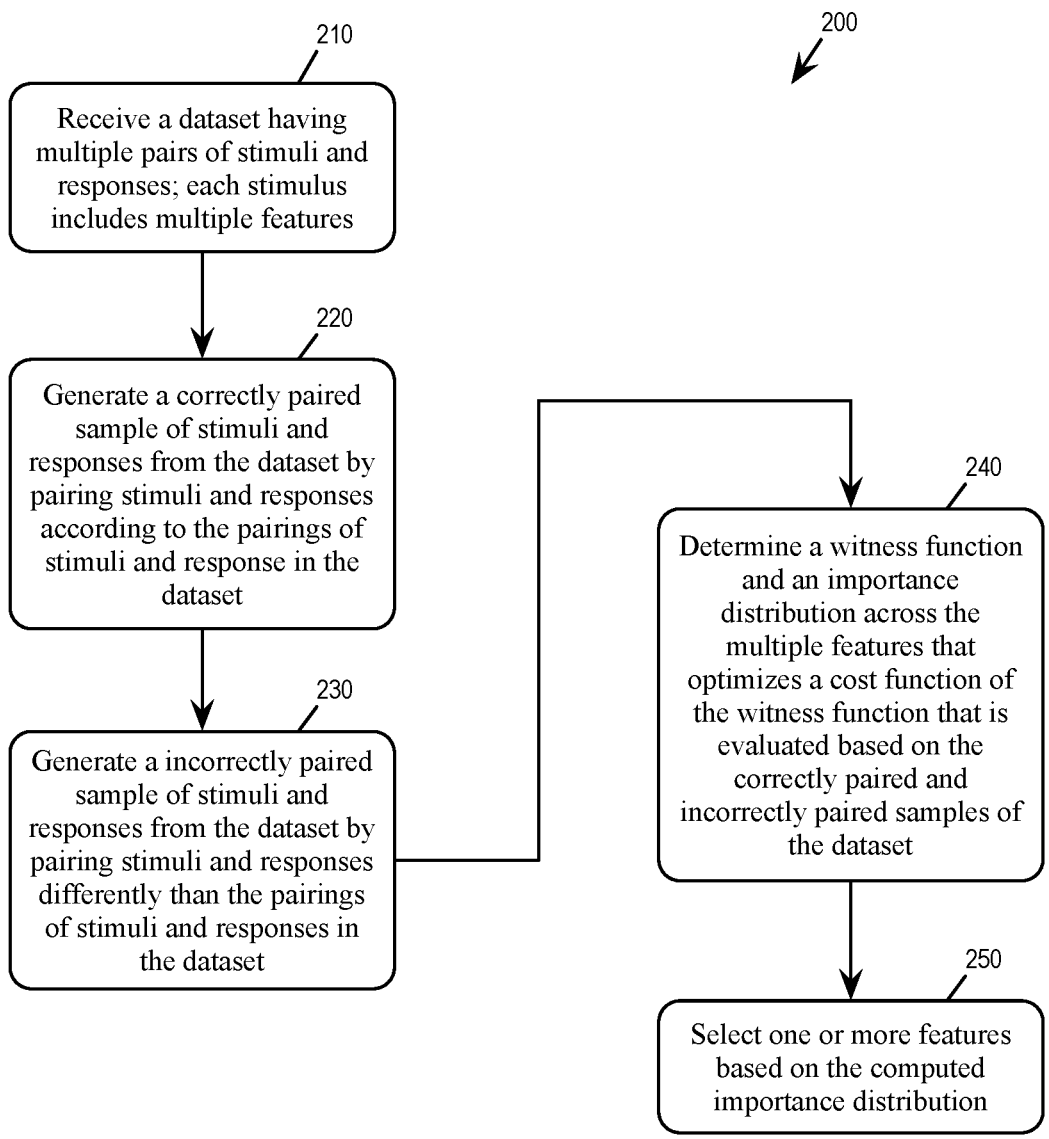
FIG. 2 conceptually illustrates a process for using SIC to perform feature selection based on a dataset.

FIG. 2 conceptually illustrates a process 200 for using SIC to perform feature selection based on a dataset. In some embodiments, one or more processing units (e.g., processor) of a computing device implementing the machine learning system 100 perform the process 200 by executing instructions stored in a computer readable medium.

The machine learning system receives (at 210) a dataset comprising multiple pairs or pairings of stimuli and responses, each stimulus including multiple features. The machine learning system generates (at 220) a correctly paired sample of stimuli and responses from the dataset by pairing stimuli and responses according to the pairings of stimuli and responses in the dataset, i.e., pairs of (x, y) for joint distribution Pxy.

The machine learning system also generates (at 230) an alternatively paired sample of stimuli and responses from the dataset by pairing stimuli and responses differently than the pairings of stimuli and responses in the dataset, e.g., by randomly pairing stimuli and responses such that (x, ỹ) simulate samples from the product of marginals PxPy. In some embodiments, each response in the alternatively paired sample is randomly paired with a stimulus from the dataset. In some embodiments, the responses from the dataset are permutated for pairing with the stimuli in the alternatively paired sample.

The machine learning system determines (at 240) a witness function and a feature importance distribution across the plurality of features that optimizes a cost function of the witness function that is evaluated based on the correctly paired and alternatively paired samples of the dataset. The cost function measures or quantifies how well the witness function is able to distinguish the correctly paired sample and the alternatively paired sample, for example, by computing a difference between a first expectation value of the witness function based on the correctly paired sample and a second expectation value of the witness function based on the alternatively paired sample. Examples of the mathematical operations that are used to determine the witness function and the feature importance distribution are described above by reference to Eq. (1) through Eq. (8).

The machine learning system selects (at 250) one or more features based on the computed feature importance distribution. For example, in some embodiments, features with importance scores higher than a certain threshold are selected for future training of machine learning systems. In some embodiments, the features are ranked according to their importance scores such that only features that rank sufficiently high are selected for future training of machine learning systems. Sections II and III below describes feature selection methods used by some embodiments of the machine learning system.

II. Feature Selection Based on Null Hypothesis

In some embodiments, the machine learning system 100 determines whether to select a particular feature j, i.e., whether the particular feature is worth selecting by testing a Null Hypothesis of conditional independence simulated by means of a held out set of samples. Specifically, the performance of a witness function $f$ for a holdout dataset is compared with the performance of the witness function $f$ for a feature j null-hypothesis dataset. The feature j null-hypothesis dataset is a dataset whose feature j is entirely independent of the response but dependent on other features (denoted as $-j$) of the dataset. The holdout dataset is a sample of the dataset 110 that were not used to determine the witness function $f$, e.g., a portion of the dataset 110 that was withheld from the machine learning system 100 when the machine learning system is determining the witness function $f$. If the witness function $f$ does not yield better result (e.g., higher mean) for the holdout dataset than for the feature j null-hypothesis dataset, the feature selection module 140 may determine to not select feature j for future machine learning operations.

In some embodiments, the witness function $f$ being tested by Null Hypothesis of conditional independence may be generated or determined by the SIC method described in Section I. However, the witness function $f$ being tested may also be generated by a traditional conventional machine learning or data fitting method that is different than SIC.

Figure 3:
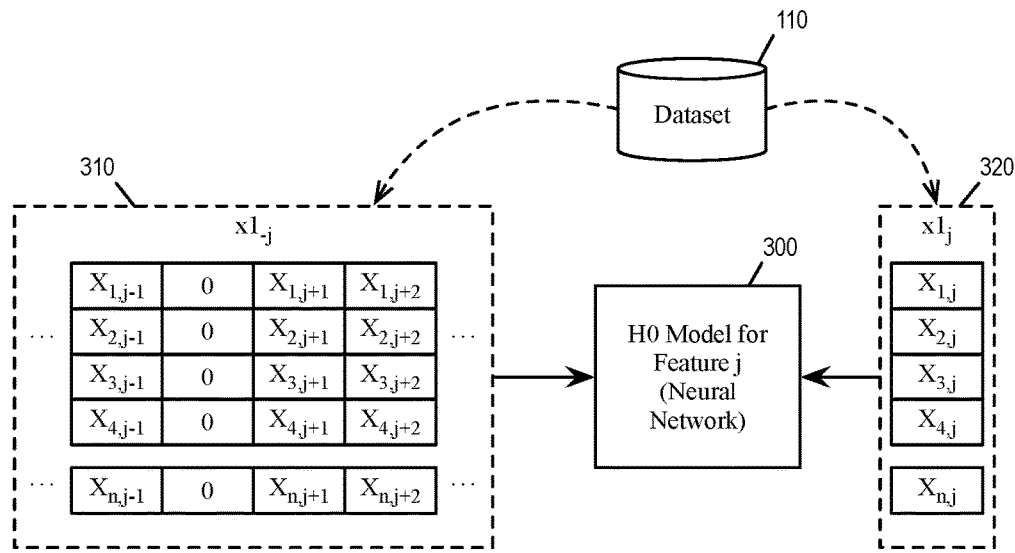
FIG. 3 conceptually illustrates training a null-hypothesis model for generating null-hypothesis data for a particular feature.

In some embodiments, the feature j null-hypothesis data is randomly generated by a machine learning model (e.g., neural network) that is trained to generate feature j based on other features (features $-j$, or features other than feature j). FIG. 3 conceptually illustrates training a null-hypothesis model for generating null-hypothesis data for a particular feature. As illustrated, the stimuli of the dataset 110 are used as training data for a null-hypothesis model 300. The values 310 of feature $-j$ (values of features other than j) from the dataset 110 are applied to the null-hypothesis model 300 as training input, and the values 320 of feature j in the dataset 110 are applied to the model as expected output. The null-hypothesis model 300 is therefore trained to generate feature j data that is (i) conditioned upon other features (features $-j$) and (ii) entirely independent of the response.

Figure 4:
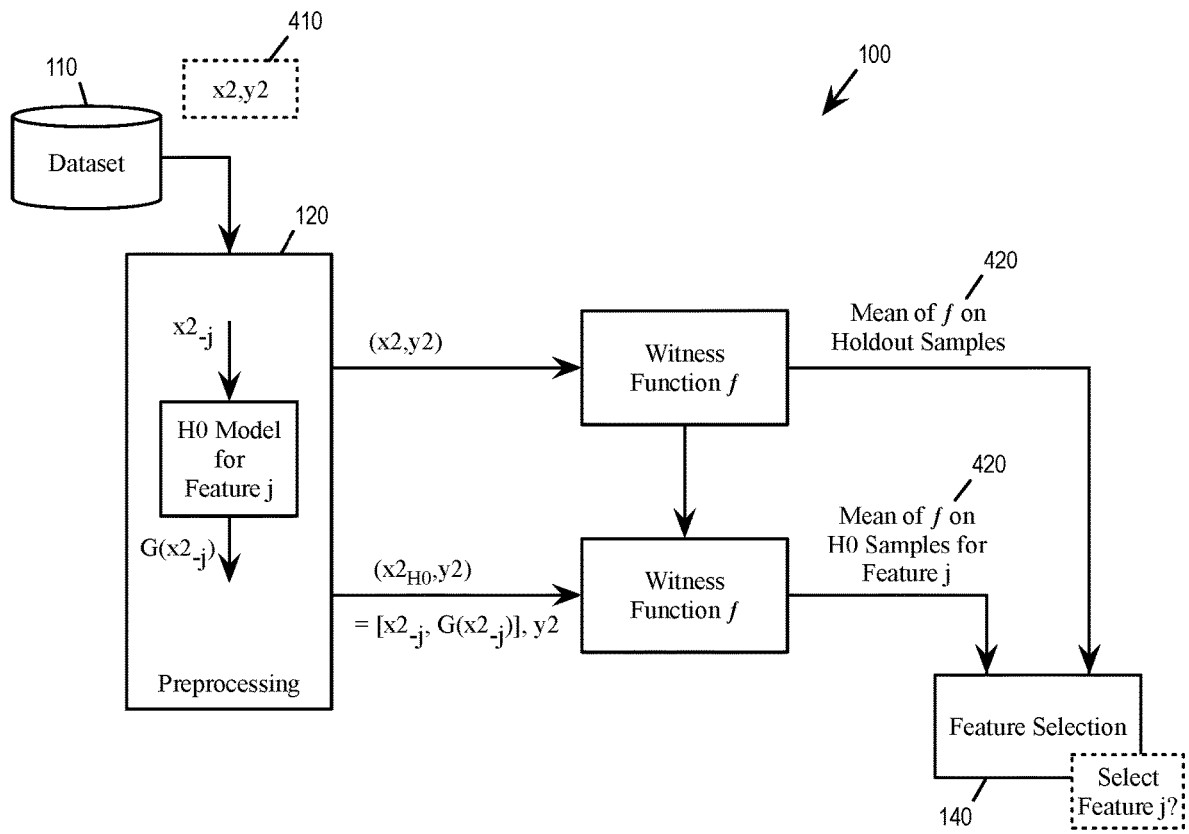
FIG. 4 conceptually illustrates using null-hypothesis data for performing feature selection.

FIG. 4 conceptually illustrates using null-hypothesis data for performing feature selection. As illustrated, the preprocessing module 120 of the machine learning system 100 implements the null-hypothesis model 300. The preprocessing module 120 receives holdout sample 410 from the dataset 110. The holdout sample 410 (denoted as x2,y2) are part of the dataset 110 that were not used for determining the witness function $f$ nor used to train the null-hypothesis model 300. The null-hypothesis model 300 uses values of features $-j$ from the holdout sample 410 (denoted as $x2_{-j}$) to produce generated feature j (denoted as $G(x2_{-j})$). The values of features $-j$ ($x2_{-j}$) together with the generated feature j ($G(x2_{-j})$) forms null-hypothesis stimulus for feature j (denoted as $x2_{H0,j}$). The null-hypothesis stimulus ($x2_{H0,j}$) together with corresponding response y2 from the holdout sample 410 are used as simulated sample (denoted as $x2_{H0,j}$,y2).

The machine learning system 100 then applies the witness function $f$ to the holdout sample 410 (x2,y2) as well as to the simulated sample for feature j ($x2_{H0,j}$,y2). The witness function $f$ is used to produce a holdout mean 420 based on the holdout sample (x2,y2). The witness function $f$ is also used to produce a null-hypothesis mean 430 based on simulated sample for feature j($x2_{H0,j}$,y2). The holdout mean 420 and the null-hypothesis mean 430 are provided to the feature selection module 140, which may decide whether to select feature j based on a comparison between the holdout mean 420 and null-hypothesis mean 430. For example, if the null-hypothesis mean 430 for feature j is better or not significantly worse than the holdout mean 420 by a certain threshold, the feature selection module 140 may decide to not select feature j since the comparison indicates that the actual data for feature j performs no better than the null-hypothesis for feature j. In some embodiments, the machine learning system 100 may also determine whether to accept the witness function $f$ based on the comparison between the holdout mean 420 and the null-hypothesis mean 430. In some embodiments, the comparison between the holdout mean 420 and the null-hypothesis mean 430 for feature j is quantified according to the following:

$$P_j = \frac{1}{M+1}\left(1 + \sum_{r=1}^{M} \mathbb{1}S_j^r > S_j\right) \qquad (9)$$

$S_j$ represents the holdout mean 420 and $S_j^r$ corresponds to value of $S_j$ obtained from a realization of the null-hypothesis 430. M represents the number of realizations of the null-hypothesis (e.g., the number of simulated samples). $P_j$ represents the probability that the null-hypothesis for feature j is true, i.e., the feature j is likely independent of the response and therefore not important. In some embodiments, if $P_j$ is greater than a certain threshold, the feature j will not be selected.

In some embodiments, the machine learning system 100 applies the process 500 to each feature of the stimuli of the dataset 110, i.e., the witness function is applied to the null-hypothesis of each feature. The features of the stimuli are ranked according to the corresponding witness function results of the null hypotheses of the features. The machine learning system 100 may select a certain number of features based on the ranking for feature selection.

Figure 5:
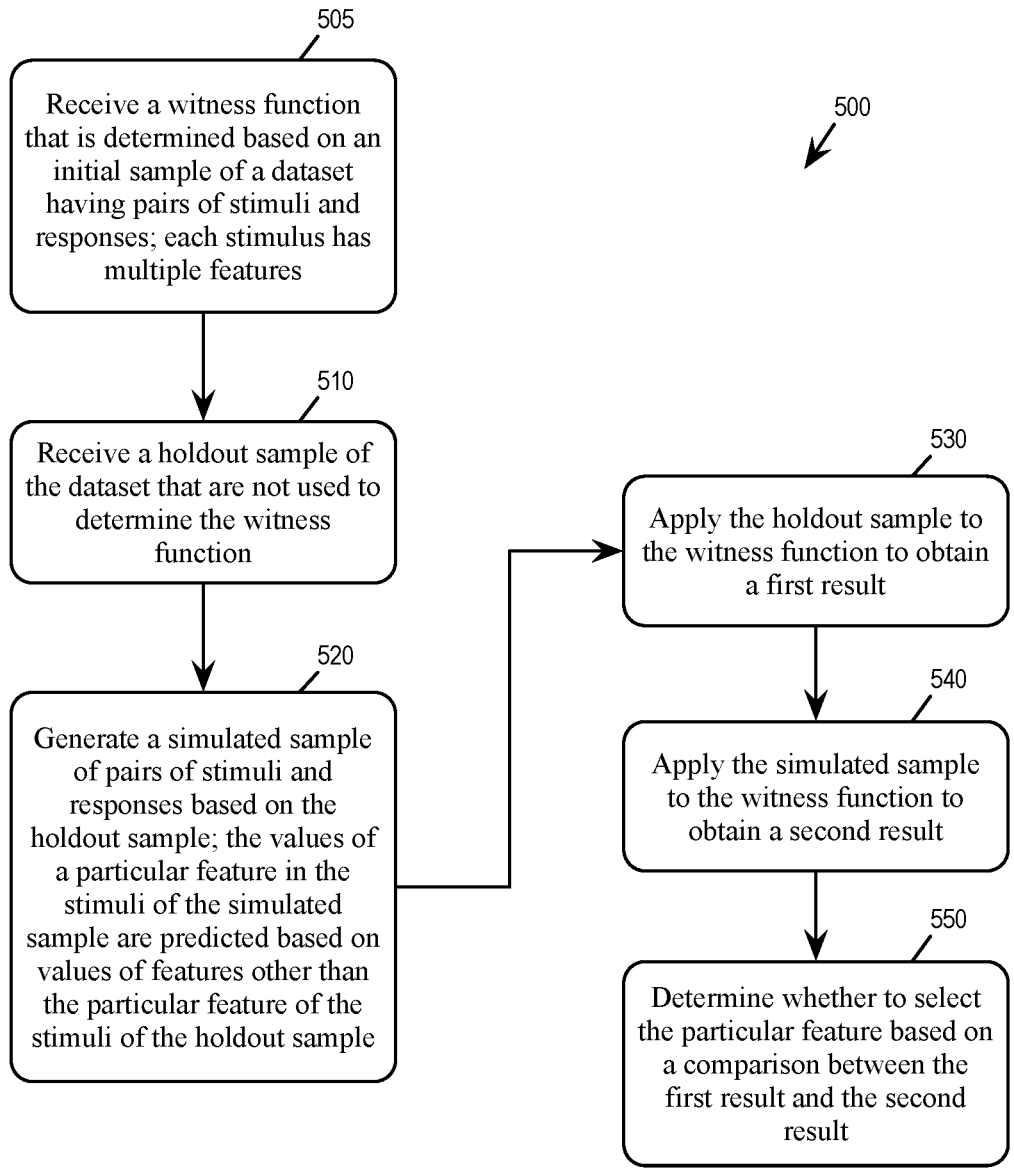
FIG. 5 conceptually illustrates a process for using null-hypothesis data for performing feature selection.

FIG. 5 conceptually illustrates a process 500 for using null-hypothesis data for performing feature selection. In some embodiments, one or more processing units (e.g., processor) of a computing device implementing the machine learning system 100 perform the process 500 by executing instructions stored in a computer readable medium.

The machine learning system receives (at 505) a witness function that is determined based on an initial sample of a dataset having pairs of stimuli and responses. Each stimulus in the pairs of stimuli and responses has multiple features. The witness function may be determined by the SIC method described in Section I or by another method.

The machine learning system receives (at 510) a holdout sample of one or more pairs of stimuli and responses (x2,y2) from the dataset that were not used to determine the witness function (e.g., not in the initial sample of the dataset). The machine learning system generates (at 520) a simulated sample of one or more pairs of stimuli and responses based on the holdout sample. The values of a particular feature (e.g., feature j) of the stimuli of the simulated sample are predicted based on values of the other features of the stimuli (e.g., features −j, or features other than the particular feature). In some embodiments, the values of the particular feature are predicted by a using a machine learning model (e.g., neural network) that is trained by values of the particular feature in the initial dataset versus the values of the other features in the initial dataset. The simulated sample (e.g., $x2_{H0,j}, y2$) corresponds to a null-hypothesis in which the value of the particular feature is entirely conditional upon other features of the stimuli but independent of the responses.

The machine learning system applies (at 530) the holdout sample to the witness function to obtain a first result (e.g., the holdout mean 420). The machine learning system also applies (at 540) the simulated sample to the witness function to obtain a second result (e.g., the null-hypothesis mean 430 for feature j.)

The machine learning system determines (at 550) whether to select the particular feature based on a comparison between the first result and the second result. For example, if the second result is better than the first result or is not significantly worse than the first result, feature selection module 140 may decide to not select the particular feature since the comparison indicates that witness function $f$ performs no better when actual data is used than when null-hypothesis data is used for the particular feature.

III. Feature Selection Based on Knockoff Data

In some embodiments, to determine whether a particular feature in the dataset 110 should be selected, the particular feature's influence score is compared with the influence score of a bogus feature of a set of control data (or knockoff data). Specifically, samples of the dataset are concatenated with the control data to create concatenated samples, and the concatenated samples are processed by SIC (at the SIC module 130) to produce influence scores for the actual features of the dataset 110 as well as for the bogus features of the control data. The influence scores of the actual features are compared with the influence scores of the bogus features to determine whether an actual feature of the dataset 110 should be selected.

Figure 6:
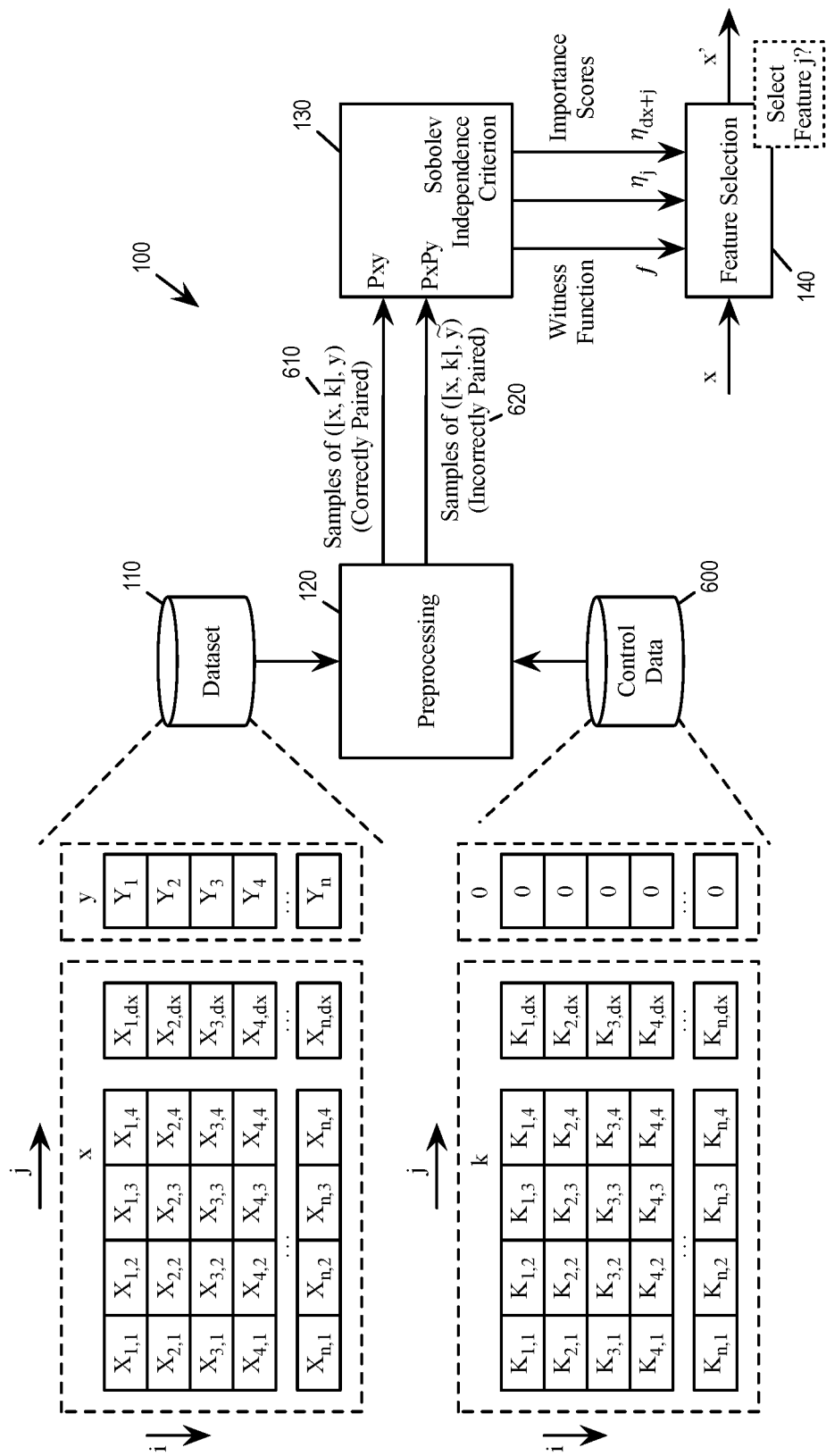
FIG. 6 conceptually illustrates using samples concatenated with control data to perform SIC for feature selection.

FIG. 6 conceptually illustrates using samples concatenated with control data to perform SIC for feature selection. As illustrated preprocessing module 120 of the machine learning system 100 receives both the dataset 110 and a set of control data 600. The preprocessing module 120 concatenates the control data 600 with correctly paired stimuli and responses of the dataset 110 as a first concatenated sample 610. The preprocessing module 120 concatenates the control data with alternatively paired stimuli and responses of the dataset 110 as a second concatenated sample 620. The SIC module 130 uses the first concatenated sample and the second concatenated sample to produce importance scores that correspond to the actual features of the dataset 110 and the bogus features of the control data 600. The feature importance scores are then used by the feature selection module 140 to perform feature selection.

The control data 600 may be a historical data that is known to not cause the response (e.g., genomes known to not have the disease). The control data 600 may be randomly selected historical data regardless of response. (The control data 600 is therefore also referred to as knockoff data.) The control data 600 is interpreted to include stimuli (denoted as k) that include values that corresponds to features of the dataset 110. Since each stimulus of the actual dataset 110 includes dx features, each stimulus of the control data 600 also includes dx features. In the figure, a feature j of a stimulus i in the control data 600 is denoted as $K_{i,j}$.

The first concatenated sample 610 includes stimuli k from the control data 600, stimuli x from the dataset 110, as well as responses y from the dataset 110 that are correctly paired with the stimuli x. The second concatenated sample 620 includes stimuli k from the control data 600, stimuli x from the dataset 110, as well as ỹ from the dataset 110 that are alternatively paired with the stimuli x.

The SIC module 130 determines a witness function $f$ and a feature importance distribution by using Sobolev Independence Criteria as described in Section I above. The first concatenated sample is used as the Pxy input (correctly paired sample) and the second concatenated sample is used as the PxPy input (alternatively paired sample) of the SIC module 130. The determined feature importance distribution η based on the first and second concatenated samples includes feature importance scores $η_j$ for j=1 . . . 2*dx, i.e., there is an importance score for each actual feature in the stimuli x and for each bogus feature in the stimuli k. In some embodiments, j=1 . . . dx are indices or positions of actual features of stimuli x while j=dx+1 . . . 2dx are bogus features of stimuli k, and each actual feature at position j has a corresponding bogus feature at position j+dx.

The feature selection module 140 in turn uses the feature importance distribution η to determine which feature to select or not select. In some embodiments, the importance score $η_j$ of each actual feature of stimuli x is compared with the importance score $η_{j+dx}$ of the corresponding bogus feature of stimuli k. The feature selection module 140 may determine to not select an actual feature at position j if its importance score $η_j$ is worse or not significantly better than the importance score $η_{j+dx}$ of the corresponding bogus feature.

By selecting the features that explain the dependency between a stimulus vector x and a response variable y, Sobolev Independence Criterion (SIC) allows interpretable decision making regarding feature selection, since SIC introduces sparsity at its input. The feature selection decision is also trustworthy and reliable because it is made with false discovery rate control. For example, instead of a black box prediction of the presence of a disease given a gene sequence, SIC predicts the presence or absence of the disease by determining a ranked list of features based on feature importance scores regarding the disease, allowing doctors to identify the genes mutation that causes the disease. SIC also improves interpretability of the result by allowing the use of highly non-linear models such as neural networks that are flexible enough to incorporate any known prior in the architecture of the network.

Figure 7:
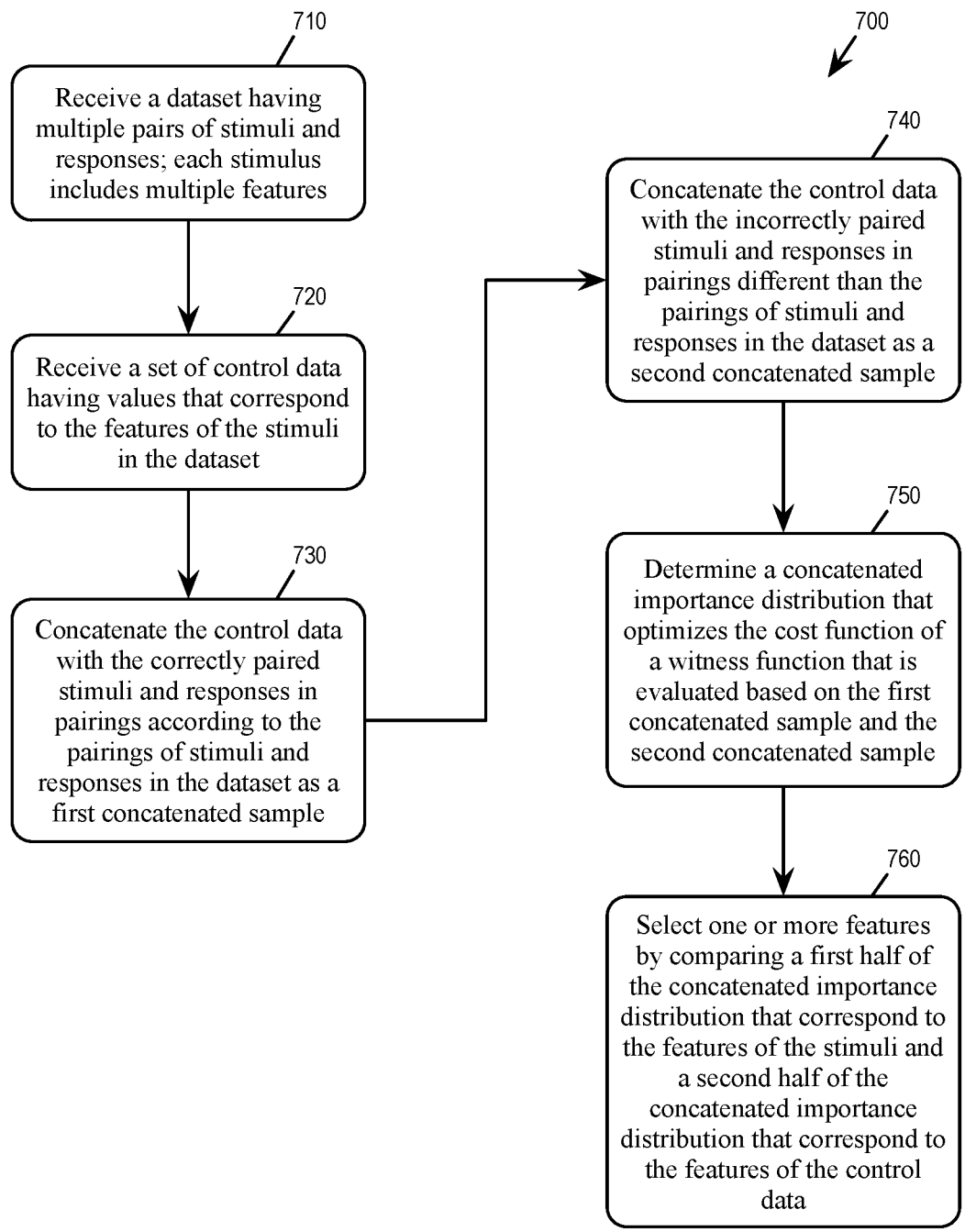
FIG. 7 conceptually illustrates a process for using samples concatenated with control data to perform feature selection.

FIG. 7 conceptually illustrates a process 700 for using samples concatenated with control data to perform feature selection. In some embodiments, one or more processing units (e.g., processor) of a computing device implementing the machine learning system 100 perform the process 700 by executing instructions stored in a computer readable medium.

The machine learning system receives (at 710) a dataset having multiple pairs or pairings of stimuli (x) and responses (y), each stimulus including multiple features. The system also receives (at 720) a set of control data (or knockoff data) having values that correspond to the multiple features. In other words, the control data is interpreted to include stimuli (k) having the same dimension (e.g., dx) as the stimuli of the dataset.

The machine learning system concatenates (at 730) the control data with correctly paired stimuli and responses from the dataset in pairings according to the pairings of stimuli and responses in the dataset as a first concatenated sample (e.g., the concatenated sample 610). The machine learning system also concatenates (at 740) the control data with alternatively paired stimuli and responses from the dataset in pairings different than the pairings of stimuli and responses in the dataset as a second concatenated sample (e.g., the concatenated sample 620).

The machine learning system determines (at 750) a concatenated feature importance distribution that optimizes the cost function of a witness function that is evaluated based on the first concatenated sample and the second concatenated sample. The cost function of the witness function measures or quantifies how well the witness function is able to distinguish the correctly paired sample and the alternatively paired sample, for example, by computing a difference between a first expectation value of the witness function based on the first concatenated sample and a second expectation value of the witness function based on the second concatenated sample. Examples of the mathematical operations that are used to determine the witness function and the feature importance distribution are described above by reference to Eq. (1) through Eq. (8) in Section I.

The machine learning system selects (at 760) one or more features by comparing a first half of the concatenated feature importance distribution that correspond to the multiple features of the stimuli and a second half of the concatenated feature importance distribution that correspond to the multiple features of the control data, e.g., by comparing the importance score $\eta_j$ of an actual feature of the stimuli of the dataset with the importance score $\eta_{j+dx}$ of a corresponding bogus feature of the control data.

By using Sobolev Independence Criterion (SIC), a computing system is able to perform feature selection on a dataset with lowered false detection rate (FDR) and improved true positive rate (TPR). The improved performance based on the SIC method has been validated on synthetic and real biological data.

The present application may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. The flowchart and block diagrams in the Figures (e.g., FIGS. 2, 5, and 7) illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 8:
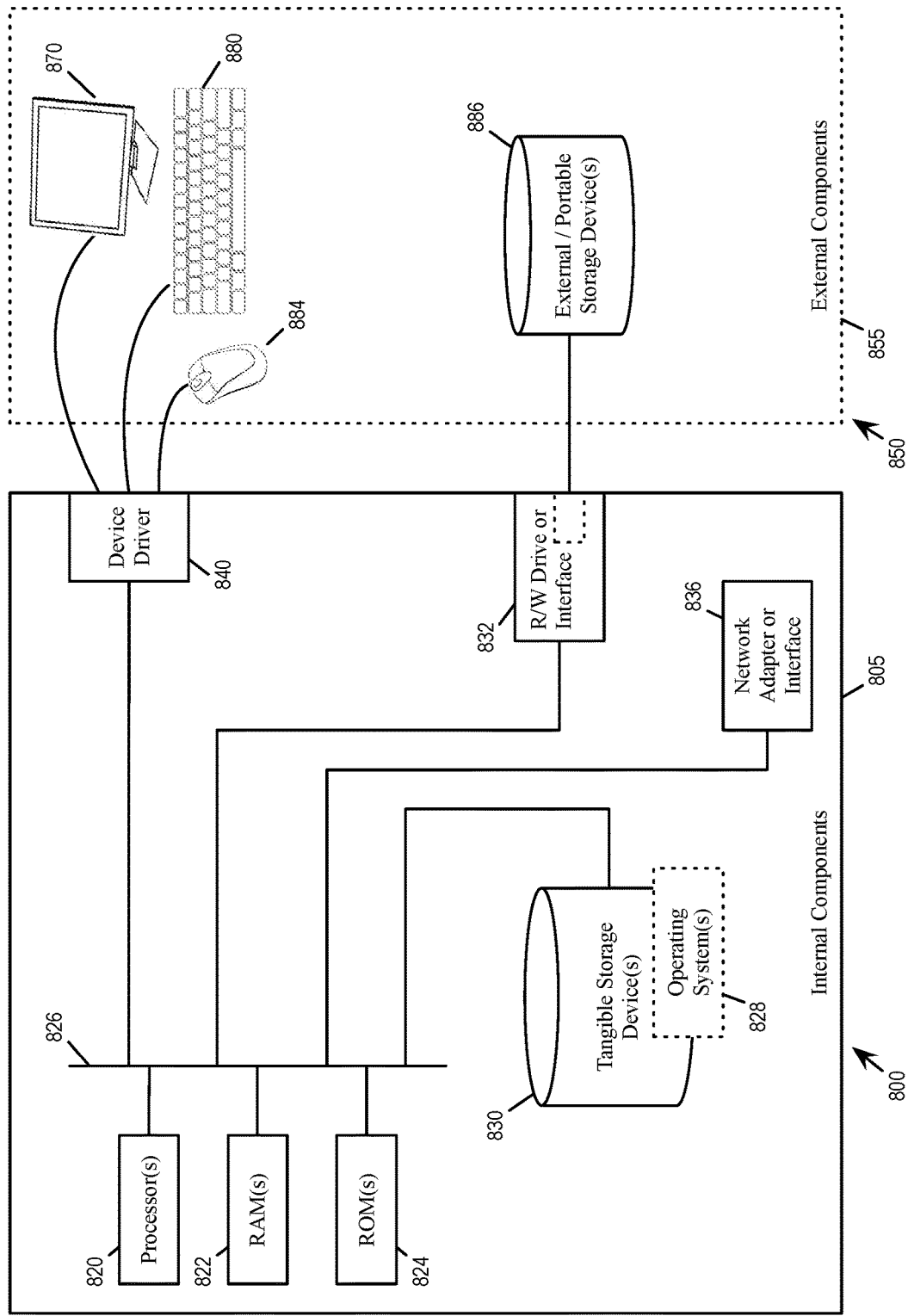
FIG. 8 shows a block diagram of the components of a data processing system in accordance with an illustrative embodiment of the present disclosure.

FIG. 8 shows a block diagram of the components of data processing systems 800 and 850 that may be used to implement a system that uses Sobolev Independence Criterion to perform feature selection (i.e., the machine learning system 100) in accordance with an illustrative embodiment of the present disclosure. It should be appreciated that FIG. 8 provides only an illustration of one implementation and does not imply any limitations with regard to the environments in which different embodiments may be implemented. Many modifications to the depicted environments may be made based on design and implementation requirements.

Data processing systems 800 and 850 are representative of any electronic device capable of executing machine-readable program instructions. Data processing systems 800 and 850 may be representative of a smart phone, a computer system, PDA, or other electronic devices. Examples of computing systems, environments, and/or configurations that may represented by data processing systems 800 and 850 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

The data processing systems 800 and 850 may include a set of internal components 805 and a set of external components 855 illustrated in FIG. 8. The set of internal components 805 includes one or more processors 820, one or more computer-readable RAMs 822 and one or more computer-readable ROMs 824 on one or more buses 826, and one or more operating systems 828 and one or more computer-readable tangible storage devices 830. The one or more operating systems 828 and programs such as the programs for executing the processes 200, 500 and 700 are stored on one or more computer-readable tangible storage devices 830 for execution by one or more processors 820 via one or more RAMs 822 (which typically include cache memory). In the embodiment illustrated in FIG. 8, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

The set of internal components 805 also includes a R/W drive or interface 832 to read from and write to one or more portable computer-readable tangible storage devices 886 such as a CD-ROM, DVD, memory stick, magnetic tape, magnetic disk, optical disk or semiconductor storage device. The instructions for executing the processes 200, 500 and 700 can be stored on one or more of the respective portable computer-readable tangible storage devices 886, read via the respective R/W drive or interface 832 and loaded into the respective hard drive 830.

The set of internal components 805 may also include network adapters (or switch port cards) or interfaces 836 such as a TCP/IP adapter cards, wireless Wi-Fi interface cards, or 3G or 4G wireless interface cards or other wired or wireless communication links. Instructions of processes or programs described above can be downloaded from an external computer (e.g., server) via a network (for example, the Internet, a local area network or other, wide area network) and respective network adapters or interfaces 836. From the network adapters (or switch port adaptors) or interfaces 836, the instructions and data of the described programs or processes are loaded into the respective hard drive 830. The network may comprise copper wires, optical fibers, wireless transmission, routers, firewalls, switches, gateway computers and/or edge servers.

The set of external components 855 can include a computer display monitor 870, a keyboard 880, and a computer mouse 884. The set of external components 855 can also include touch screens, virtual keyboards, touch pads, pointing devices, and other human interface devices. The set of internal components 805 also includes device drivers 840 to interface to computer display monitor 870, keyboard 880 and computer mouse 884. The device drivers 840, R/W drive or interface 832 and network adapter or interface 836 comprise hardware and software (stored in storage device 830 and/or ROM 824).

The foregoing one or more embodiments implements a machine learning system within a computer infrastructure by having one or more computing devices implementing Sobolev Independence Criterion and generating influence scores for features of dataset. The computer infrastructure is further used to perform feature selection based on generated influence score, which may involve using the computer infrastructure to generate null hypothesis samples and concatenated samples.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
receiving a dataset comprising pairings of stimuli and responses, each stimulus comprising a plurality of features;
generating a correctly paired sample of stimuli and responses from the dataset by pairing stimuli and responses according to the pairings of stimuli and responses in the dataset;
generating an alternatively paired sample of stimuli and responses from the dataset by pairing stimuli and responses differently than the pairings of stimuli and responses in the dataset;
determining a witness function and a feature importance distribution across the plurality of features that optimizes a cost function that is evaluated based on the correctly paired sample and the alternatively paired sample of the dataset; and
selecting one or more features based on the feature importance distribution.

2. The computer-implemented method of claim 1, wherein:
a stimulus in a pairing represents a list of genes of an individual,
a response in a pairing represents a presence of a particular phenotype in the individual, and
a feature in the stimulus represents a gene of the individual.

3. The computer-implemented method of claim 1, wherein determining the feature importance distribution comprises evaluating partial derivatives of the witness function at each feature of the plurality of features.

4. The computer-implemented method of claim 1, wherein the cost function measures how well the witness function is able to distinguish the correctly paired sample and the alternatively paired sample.

5. The computer-implemented method of claim 4, wherein:
the cost function comprises a gradient sparsity term and a regularization term, and
the gradient sparsity term is evaluated by computing a partial derivative of the witness function at each feature of the plurality of features.

6. The computer-implemented method of claim 5, wherein the determined witness function and feature importance distribution minimizes the gradient sparsity term.

7. The computer-implemented method of claim 1, further comprising:
receiving a holdout sample of one or more pairs of stimuli and responses from the dataset that were not used to determine the witness function;
generating a simulated sample of one or more pairs of stimuli and responses based on the holdout sample, wherein values of a particular feature of the stimuli of the simulated sample are predicted based on values of features other than the particular feature of the stimuli of the simulated sample;
applying the holdout sample to the witness function to obtain a first result;
applying the simulated sample to the witness function to obtain a second result; and
determining whether to select the particular feature based on a comparison between the first result and the second result.

8. The computer-implemented method of claim 7, wherein the values of the particular feature are predicted by using a machine learning model that is trained by values of the particular feature versus the values of the features other than the particular feature.

9. A computing device comprising:
a processor; and
a storage device storing a set of instructions, wherein an execution of the set of instructions by the processor configures the computing device to perform acts comprising:
receiving a dataset comprising pairings of stimuli and responses, each stimulus comprising a plurality of features;
generating a correctly paired sample of stimuli and responses from the dataset by pairing stimuli and responses according to the pairings of stimuli and responses in the dataset;
generating an alternatively paired sample of stimuli and responses from the dataset by pairing stimuli and responses differently than the pairings of stimuli and responses in the dataset;
determining a witness function and a feature importance distribution across the plurality of features that optimizes a cost function that is evaluated based on the correctly paired sample and the alternatively paired sample of the dataset; and
selecting one or more features based on the feature importance distribution.

10. The computing device of claim 9, wherein:
a stimulus in a pairing represents a list of genes of an individual,
a response in a pairing represents a presence of a particular phenotype in the individual, and
a feature in the stimulus represents a gene of the individual.

11. The computing device of claim 9, wherein determining the feature importance distribution comprises evaluating partial derivatives of the witness function at each feature of the plurality of features.

12. The computing device of claim 9, wherein the cost function measures how well the witness function is able to distinguish the correctly paired sample and the alternatively paired sample.

13. The computing device of claim 12, wherein:
the cost function comprises a gradient sparsity term and a regularization term, and
the gradient sparsity term is evaluated by computing a partial derivative of the witness function at each feature of the plurality of features.

14. The computing device of claim 13, wherein the determined witness function and feature importance distribution minimizes the gradient sparsity term.

15. The computing device of claim 9, wherein an execution of the set of instructions by the processor further configures the computing device to perform acts comprising:
receiving a holdout sample of one or more pairs of stimuli and responses from the dataset that were not used to determine the witness function;
generating a simulated sample of one or more pairs of stimuli and responses based on the holdout sample, wherein values of a particular feature of the stimuli of the simulated sample are predicted based on values of features other than the particular feature of the stimuli of the simulated sample;
applying the holdout sample to the witness function to obtain a first result;
applying the simulated sample to the witness function to obtain a second result; and
determining whether to select the particular feature based on a comparison between the first result and the second result.

16. The computing device of claim 15, wherein the values of the particular feature are predicted by using a machine learning model that is trained by values of the particular feature versus the values of the features other than the particular feature.

17. A computer program product comprising:
one or more non-transitory computer-readable storage devices and program instructions stored on at least one of the one or more non-transitory storage devices, the program instructions executable by a processor, the program instructions comprising sets of instructions for:
receiving a dataset comprising pairings of stimuli and responses, each stimulus comprising a plurality of features;
receiving a set of control data having values that correspond to the plurality of features;
concatenating the control data with correctly paired stimuli and responses from the dataset in pairings according to the pairings of stimuli and responses in the dataset as a first concatenated sample;
concatenating the control data with alternatively paired stimuli and responses from the dataset in pairings different than the pairings of stimuli and responses in the dataset as a second concatenated sample;
determining a concatenated feature importance distribution that optimizes a cost function that is evaluated based on the first concatenated sample and the second concatenated sample; and
selecting one or more features by comparing a first half of the concatenated feature importance distribution that correspond to the plurality of features of the stimuli and a second half of the concatenated feature importance distribution that correspond to the plurality of features of the control data.

18. The computer program product of claim 17, wherein determining the feature importance distribution comprises evaluating partial derivatives of the witness function at each feature of the plurality of features.

19. The computer program product of claim 17, wherein the cost function measures how well the witness function distinguishes the first concatenated sample from the second concatenated sample.

20. The computer program product of claim 19, wherein:
the cost function comprises a gradient sparsity term and a regularization term,
the gradient sparsity term is evaluated by computing a partial derivative of the witness function at each feature of the plurality of features, and
the determined witness function and feature importance distribution minimizes the gradient sparsity term.

\* \* \* \* \*